United States Patent
Ackermann et al.

(10) Patent No.: US 9,527,117 B2
(45) Date of Patent: Dec. 27, 2016

(54) METHOD FOR CLEANING RESPIRATORS

(71) Applicant: MEIKO Maschinenbau GmbH & Co. KG, Offenburg (DE)

(72) Inventors: Frank Ackermann, Frieshenheim (DE); Markus Braun, Offenburg (DE); Thomas Peukert, Bühl (DE); Hans-Josef Rauber, Oberhamersbach (DE); Marijan Simundic, Ohlsbach (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 0 days.

(21) Appl. No.: 15/057,496

(22) Filed: Mar. 1, 2016

(65) Prior Publication Data

US 2016/0175892 A1 Jun. 23, 2016

Related U.S. Application Data

(63) Continuation of application No. 13/682,302, filed on Nov. 20, 2012, now Pat. No. 9,308,558, which is a continuation of application No. PCT/EP2011/057706, filed on May 12, 2011.

(30) Foreign Application Priority Data

May 21, 2010 (DE) .................. 10 2010 029 221

(51) Int. Cl.
*B08B 3/10* (2006.01)
*B08B 7/00* (2006.01)
(Continued)

(52) U.S. Cl.
CPC .............. *B08B 3/024* (2013.01); *A61L 2/16* (2013.01); *A62B 23/025* (2013.01); *A62B 25/00* (2013.01);
(Continued)

(58) Field of Classification Search
CPC ........ A47L 15/0078; A62B 25/00; A61L 2/16; B08B 3/02; B08B 3/04; B08B 3/10; B08B 13/00; B08B 3/08; B08B 5/00
See application file for complete search history.

(56) References Cited

U.S. PATENT DOCUMENTS

| 3,881,503 A | 5/1975 | Fox et al. |
| 4,354,514 A | 10/1982 | Sundheimer |

(Continued)

FOREIGN PATENT DOCUMENTS

| DE | 11 74 169 B | 7/1964 |
| DE | 298 22 172 U1 | 2/1999 |

(Continued)

OTHER PUBLICATIONS

English Translation of the International Search Report, PCT/EP2011/057706, Dated Sep. 10, 2012.
(Continued)

*Primary Examiner* — Alexander Markoff
(74) *Attorney, Agent, or Firm* — Bose McKinney & Evans LLP

(57) ABSTRACT

The present disclosure provides a method for cleaning a respirator using a cleaning device of the type having a fluid device and a pressure application device. The method comprises applying a cleaning fluid to the respirator with the fluid device; connecting a gas carrying element of the respirator to a pressure connection of the pressure application device; and applying pressurized gas to the gas carrying element during the application of the cleaning fluid.

35 Claims, 2 Drawing Sheets

(51) Int. Cl.
*B08B 3/02* (2006.01)
*A62B 25/00* (2006.01)
*B08B 3/04* (2006.01)
*B08B 5/00* (2006.01)
*A61L 2/16* (2006.01)
*B08B 13/00* (2006.01)
*B08B 3/08* (2006.01)
*A62B 23/02* (2006.01)
*A47L 15/00* (2006.01)

(52) U.S. Cl.
CPC . *B08B 3/02* (2013.01); *B08B 3/04* (2013.01); *B08B 3/08* (2013.01); *B08B 3/10* (2013.01); *B08B 5/00* (2013.01); *B08B 13/00* (2013.01); *A47L 15/0078* (2013.01); *A61B 90/70* (2016.02)

(56) References Cited

U.S. PATENT DOCUMENTS

| | | |
|---|---|---|
| 4,552,728 A | 11/1985 | Taylor |
| 5,664,594 A | 9/1997 | Kee |
| 6,334,341 B1 | 1/2002 | Hellhake et al. |
| 6,571,811 B2 | 6/2003 | Kabboush |
| 7,124,766 B1 | 10/2006 | Hedgpeth |
| 2005/0274624 A1 | 12/2005 | Arata |
| 2009/0050181 A1 | 2/2009 | Johansson |
| 2009/0183753 A1 | 7/2009 | Maennle et al. |
| 2010/0175726 A1 | 7/2010 | Eli |

FOREIGN PATENT DOCUMENTS

| | | |
|---|---|---|
| DE | 200 03 744 U1 | 7/2000 |
| DE | 200 03 743 U1 | 11/2000 |
| DE | 100 20 835 A1 | 11/2001 |
| DE | 10 2005 033 618 B3 | 11/2006 |
| DE | 10 2007 009 936 A1 | 9/2008 |
| DE | 10 2007 012 768 B4 | 1/2009 |
| EP | 1 088 928 A1 | 4/2001 |
| EP | 0 935 687 B1 | 6/2001 |

OTHER PUBLICATIONS

English Translation of the International Preliminary Report on Patentability and Written Opinion of the International Searching Authority, PCT/EP2011/057706, Dated Dec. 13, 2012.

METHOD FOR CLEANING RESPIRATORS

RELATED APPLICATIONS

This application is a continuation of U.S. patent application Ser. No. 13/682,302, filed Nov. 20, 2012, which is a continuation of PCT/EP2011/057706, filed May 12, 2011, which claims priority to DE 10 2010 029 221.4, filed May 21, 2010, all of which are hereby incorporated by reference in their entireties.

BACKGROUND

The invention relates to a cleaning device for cleaning and optionally also additionally disinfecting respirators or component parts of respirators. The invention also relates to a holder for use in a cleaning device and to a use of a cleaning device and to a method for cleaning respirators. Such devices and methods are generally used for cleaning respirators or component parts of the same, for example respirators for members of rescue teams such as firefighters, technical aid agencies or paramedics, respirators for divers or generally people who work in hostile or critical environments and for members of military forces and security forces, such as for example the police. The proposed devices and methods can also be used for respirators in the medical sector, for example breathing masks for supplying oxygen and for carrying out operations. In particular, the cleaning of breathing masks or breathing regulators in general comes into consideration as an area of use.

Respirators, such as for example protective breathing masks or breathing regulators, generally form part of the personal protective equipment of members of rescue teams, military forces or security forces. For instance, many respirators for various intended uses are known from the prior art. For example, members of rescue teams such as firefighters use protective breathing masks with filters for removing harmful constituents from the respiratory air that is taken in. In many cases, however, a device known as a breathing regulator is used as an alternative or in addition to a filter, allowing the user to be ventilated with a respiratory gas, for example compressed air. Breathing regulators generally enable a user to breathe from a pressurized gas cylinder or some other pressurized gas connection and in this way stay under water, for example, or in some other atmosphere that cannot be breathed in or is toxic. For this purpose, the pressurized gas, for example compressed air, from the pressurized gas connection is adapted by the breathing regulator to a pressure prevailing in the user's working environment.

After each time they are used, the respirators or component parts of the same must generally be cleaned, hygienized, dried, checked, and repaired if necessary, and packed. The cleaning is intended to remove all contamination as a result of use or storage, so that the respirators can be provided in a macroscopically clean and hygienically satisfactory state, for example for the next steps of preparation. These requirements generally also apply to other component parts of respirators, such as for example add-on and accessory parts of breathing masks, such as for example filters or breathing regulators. Since respirators or the component parts thereof are generally safety devices, a number of requirements have to be observed when cleaning these devices. Apart from adequate cleaning and hygienization, in many cases it is for example necessary to ensure that accessory parts remain assigned to the respective breathing masks for technical reasons. Furthermore, there is generally the requirement that gas carrying regions of certain elements of respirators, for example gas carrying regions of breathing regulators, must not come into contact with cleaning fluid, for example water and/or cleaning solution.

In many cases, respirators, such as for example breathing masks and accessories thereof, are either cleaned manually or in modified laundry washing machines with the aid of protective bags and/or with the aid of adapters. For example, EP 0 935 687 B1 generally discloses a washing machine which has a tub with a drum. A shell of the drum has a bulged structure directed toward the interior of the drum, with holes at corner points of outer contours of the bulging directed toward the exterior of the drum. With such washing machines it is possible in principle to clean items of equipment for members of rescue teams particularly gently.

EP 1 088 928 A1 discloses a holding system for protective breathing masks in a laundry treatment machine. The holding system has a carrying strut, which is arranged in a drum of the laundry treatment machine to rotate therewith, and to which the protective breathing masks can be connected.

DE 200 03 743 U1 and DE 298 22 172 U1 respectively disclose devices for treating protective suits. In these cases, clothes hangers which comprise flexible air outlet nozzles are used. The clothes hangers are respectively fastened to a pivoting device. Cleaning of respirators is generally not possible, or only with difficulty, by means of the devices shown.

DE 10 2005 033 618 B3 discloses a device for cleaning protective breathing masks. The device comprises a closable housing and at least one receptacle for at least one protective breathing mask, arranged in a carrier. Also provided are a nozzle arrangement and a brush arrangement, a movement of the protective breathing masks allowing them to be brushed. However, an individual assignment and cleaning of accessory parts of masks is not possible by means of the device disclosed. Furthermore, the cleaning of gas carrying elements, such as for example breathing regulators, is not possible with the device disclosed. DE 200 03 744 U1 also discloses a device for cleaning, disinfecting and drying protective breathing masks that has a carrying frame with an assigned nozzle system and individual treatment locations. This device is also not suitable in principle for cleaning gas carrying elements and accessory parts.

DE 10 2007 009 936 A1 discloses a cleaning device for compressed air respirators. This device has a receiving space bounded by a protective grid and rotating nozzle carriers. The nozzle carriers are in this case located outside the protective grid. However, a disadvantage of the device presented is that cleaning liquid can penetrate into gas carrying regions.

By contrast, the cleaning of sensitive components of respirators, such as for example breathing regulators, is generally performed manually. If necessary, manual cleaning can be assisted by placement in ultrasonic cleaning devices. However, DE 10 2007 012 768 B4 discloses a method and a device for cleaning breathing regulators. In this case, the items to be cleaned are fitted onto holders of a rotating element and repeatedly immersed in a liquid bath with cleaning liquid, disinfecting liquid and rinsing liquid. In this case, to seal them, breathing respirators first have compressed air applied to them between the valve and the tube connection and are then immersed in the liquid bath. However, a disadvantage of such immersion methods is that complex holders with corresponding actuators are required in order to ensure by appropriate movements that cleaning fluid is removed from the various cavities after cleaning.

From the associated medical field, washers in which ventilating tubes can be rinsed are also known. Such washers are generally designed as single-circuit machines, also referred to as water-changing machines. This means that the washers have a rinsing container, in which the cleaning and the conditioning of the cleaning liquid take place. For changing a cleaning liquid, for example for changing from a washing liquid to a final rinsing liquid, a complete change of the water within the container is required.

The known methods and devices for cleaning respirators, such as for example protective breathing masks and the accessory parts thereof, have many disadvantages. For instance, manual cleaning of the respirators is very labor-intensive. Moreover, the cleaning process is in this case greatly influenced by the individual cleaning force and, as a result, can scarcely be standardized.

By contrast, the cleaning in modified laundry washing machines is comparatively time-intensive. Moreover, after cleaning, the respirators or component parts thereof are in many cases filled inside with cleaning fluid, since they are either arbitrarily arranged in the drum of the washing machine or since their position within the drum is fixed and cannot be specifically influenced, so that the respirators generally cannot drain when the cleaning procedure is ended. Accessory parts usually cannot be cleaned at the same time in the washing machine, since during the process they often become detached from the item to which they are individually assigned.

Particularly critical with the known methods and devices is the cleaning of gas carrying elements of the respirators, such as for example one or more pipelines, tubes or valves and/or breathing regulators. For such breathing regulators, so far only a few automated cleaning methods that would satisfy the aforementioned safety requirements have been available. On the other hand, the cleaning method known from DE 10 2007 012 768 B4 has the aforementioned disadvantages and is comparatively complex. Furthermore, the device presented does not at the same time make it possible to clean, and if necessary disinfect, breathing regulators and protective breathing masks as well as accessory parts. Washers from the associated medical field that have been adapted for cleaning masks are not suitable either for cleaning and sufficiently hygienizing breathing regulators.

SUMMARY

The present invention provides devices and methods for cleaning and optionally additionally disinfecting respirators that address the aforementioned disadvantages. These teachings also to make it possible for gas carrying elements of respirators, such as for example gas carrying elements with at least one internal valve, such as for example breathing regulators, to be cleaned reliably, quickly and nevertheless in a way that satisfies all safety requirements.

In one aspect of this disclosure, a cleaning device for cleaning and also optionally additionally disinfecting respirators is disclosed. Respirators are understood here as meaning generally devices which are in some way set up for providing respiratory gas to at least one human and/or animal user. These respirators may in this case be complete, ready-to-operate respirators, or else component parts of the same, so that no distinction is made hereafter between respirators and the component parts thereof. In particular, the respirators may be breathing masks, protective breathing masks, tubes, valves, filters, pressurized gas containers, breathing regulators or combinations of the elements mentioned and/or other elements.

The cleaning device comprises at least one cleaning chamber for receiving at least one respirator. This cleaning chamber may in principle be designed as a cleaning chamber that is closed, open or can be opened. The cleaning chamber may be enclosed on all sides, or at least in two dimensions, by a housing, which may be of a completely closed design, but in principle may also have one or more apertures. The cleaning chamber may, in particular, be designed as a rigid cleaning chamber, that is to say as a cleaning chamber which does not change its position and/or alignment during a cleaning process, but may in principle also be designed as a movable cleaning chamber, for example as a pivotable and/or rotatable cleaning chamber, which changes its position and/or orientation during a cleaning process in the cleaning device, for example by a pivoting action, a rotation, a spinning process, a vibrating process or similar movements. To this extent, the cleaning chamber may, for example, be designed as a washing chamber of a washer and the cleaning device may be designed as a washer, and/or the cleaning chamber may be designed as a drum of a washing machine, and the cleaning device may be in the form of a washing machine. For example, dishwashers and/or laundry washing machines of a commercial type or for the domestic sector may be modified according to this disclosure.

The cleaning device also comprises at least one fluid device for applying at least one cleaning fluid to the respirator. A cleaning fluid should in this case be understood as meaning in principle any desired liquid and/or in principle any desired gas that can have a macroscopically and/or microscopically cleaning effect on the respirator. A fluid device should be understood as meaning generally a device by means of which the cleaning fluid can be applied directly or indirectly in any desired way to the respirator received within the cleaning chamber. This may take place for example in the form of direct application, for example by spraying, sprinkling, jetting or a combination of the direct types of application mentioned and/or other types in which cleaning fluid emerging from the fluid device impinges directly on the respirator. This kind of application may be performed in particular in the case of a fixed cleaning chamber, for example in the case of a washer. Alternatively or in addition, the application by means of the fluid device may also be performed in such a way that the fluid device completely or partially fills the cleaning chamber with cleaning fluid, so that, at least in one position of the cleaning chamber, the cleaning fluid received in the cleaning chamber comes into contact with the cleaning fluid. This kind of application may be used in particular in the case of a design of the cleaning chamber as a movable cleaning chamber, for example in the form of a drum. Combinations of the types of application mentioned and/or other types of application are also possible. Irrespective of whether the cleaning chamber is designed rigidly or movably, the application of the cleaning fluid may be performed in the simple operating mode, in that the cleaning fluid is applied to the respirator only once. Alternatively or in addition, however, cleaning may also be performed in a circulating operating mode, in that cleaning fluid is applied repeatedly to the respirator. Such circulating operating modes and circulating circuits are known for example from conventional washers or washing machines.

The cleaning device also has at least one pressure application device with at least one pressure connection. A pressure application device is understood as meaning generally a device which is set up to allow it to provide a fluid, in particular a gas, at a pressure above standard pressure, for example a pressure of at least 1.5 bar, preferably a pressure of at least 2 bar. A pressure connection should be understood in principle as meaning any desired connection of the pressure application device by way of which the fluid, in particular the gas, can be provided to the pressure application device. In particular, this pressure connection may be arranged inside the cleaning chamber and/or be accessible from inside the cleaning chamber. Provision of a plurality of pressure connections is also conceivable. It is intended that the pressure connection can be connected to at least one gas carrying element of the respirator in the cleaning chamber, preferably to a number of gas carrying elements of a number of respirators in the cleaning chamber. A gas carrying element should be understood in this case as meaning generally an element to which a respiratory gas is applied during use of the respirator by a human or animal user or which can in some other way come into contact with the respiratory gas. In particular, it may be a breathing regulator and/or a respiratory tube with at least one valve. In particular, the gas carrying element may be an element which has at least one tube and/or at least one other type of gas carrying device with an inner space and/or at least one valve, to which generally cleaning fluid must not be applied. For example, the gas carrying element may be a region of the respirator to which a pressure above standard pressure is applied during operation, for example a gas carrying region of a respirator above a standard pressure, for example above 1.5 bar, in particular above 2 bar. It may, in particular, be a respiratory gas carrying region of a breathing regulator, it being possible in principle for the breathing regulator to be a single-stage or else multi-stage breathing regulator. In this case, the gas carrying element may be, for example, part of a first stage and/or a second stage and/or possibly further stages of the breathing regulator or else a complete breathing regulator. For example, the gas carrying element may be a region between a tube connection and a valve of a breathing regulator, or the gas carrying element may comprise such a region. A connection between the pressure connection and the gas carrying element should be understood as meaning generally a fluidic connection, in particular a gas connection, so that the fluid under pressure of the pressure application device can be transferred into the gas carrying element of the respirator, in particular into an inner space of the gas carrying element, preferably without any fluid loss and/or pressure loss occurring in this connection. In addition, the connection between the pressure connection and the gas carrying element of the respirator may optionally comprise at least one mechanical connection, in particular a positive and/or non-positive connection, so that the respirator can be fixedly connected to the pressure connection. For example, it may be a screw connection and/or a clamping connection and/or a tensioning connection, for which purpose the pressure connection and/or the respirator may in each case have at least one mechanical connecting element. It may, in particular, be a plug-in connection in the form of a quick coupling and/or a thread, for example a coupling piece for a respiratory connection of a breathing regulator. A quick connection should be understood in this case as meaning generally a gas-tight and/or liquid-tight plug-in connection between two fluid carrying components which can be mechanically secured by a mechanical fixing that can be established and released in a simple and quick way, in particular without use of a screw closure, for example by at least one clip and/or a bayonet closure and/or a screw closure, for example a union nut. The connection can in particular be established without a tool. In particular, the pressure connection may comprise a plurality of adapters of a fixed or exchangeable design for connection to different types of gas carrying elements. By means of these adapters, a plurality of different gas carrying elements may be able to be connected directly or indirectly to the pressure connection, for example different types and/or kinds of gas carrying elements, for example of different makes or manufacturers. For example, a set of adapters with a plurality of different coupling pieces (for example coupling pieces of a quick coupling) and/or threads may be provided for the connection of different gas carrying elements. For example, they may be different quick coupling systems and/or standard threads. Alternatively or in addition, the at least one pressure connection may, however, also be designed as a fixed pressure connection for a specific type of connecting element or for a specific type of gas carrying element. It is particularly advantageous if the pressure connection and/or the coupling system is set up in such a way that on the one hand no gas can escape when no counterpart is connected, and that in this case no other medium, for example cleaning fluid, can enter the gas carrying element either.

The pressure application device is set up for applying pressurized gas to the gas carrying element. A pressurized gas should be understood in this case as meaning generally any desired gas that has a pressure above standard pressure, that is to say a pressure above 1 bar. It may, in particular, be a pressure above 1.5 bar, in particular above 2 bar, and particularly preferably above 3 bar. Particularly preferably, the pressure application device is set up in such a way that the pressure application of the pressurized gas is performed in such a way that all the cleaning fluid is kept away from an inner space of the respirator to which the pressurized gas is applied. The pressurized gas may be, for example, compressed air or some other gaseous medium at a positive pressure, for example nitrogen, carbon dioxide or the like. In particular, an inert gas may be used as the pressurized gas. The cleaning device may, in particular, be designed in such a way that the pressure application by way of the pressure application device is performed during at least one cleaning process, for example during at least one program step of a single-step or multi-step cleaning program. In particular, the application of the pressurized gas may be performed at the same time as the cleaning fluid is applied to the respirator. The pressure connection may accordingly be arranged in particular within the cleaning chamber, so that the simultaneous application of pressurized gas and cleaning fluid can take place.

The cleaning device may be advantageously developed in various ways. For instance, as stated above, the pressure connection may comprise at least one positive and/or non-positive connecting element, in order additionally to establish a mechanical connection to the respirator. This may, in particular, be a quick-coupling system and/or a thread. Alternatively or in addition, other mechanical connecting elements can also be used.

The cleaning device may, in particular, be designed as a single-chamber washer and/or comprise a single-chamber washer. A single-chamber washer should be understood in this case as meaning a washer with a single cleaning chamber, in which preferably a number of program steps of a multi-stage cleaning program can be carried out. The application within a single-chamber washer may be performed in particular by a fluid device in the form of one or more nozzles, for example in the form of one or more spraying nozzles and/or other nozzles, for example rigid and/or rotatable and/or pivotable nozzle arms. The single-chamber washer may be designed in particular as what is known as a multi-circuit washer. Accordingly, the single-chamber washer may, for example, have at least one fluid tank that is formed separately from the cleaning chamber, it being possible for at least one cleaning fluid to be conditioned, for example heated and/or provided with additives, in the fluid tank independently of a cleaning process proceeding at the time in the cleaning device. Such washers with a multi-circuit principle are known from the area of industrial dishwashers, in which a tank for conditioning a post-rinsing liquid, for example a boiler and/or a tank with a continuous heater, is generally provided independently of the cleaning chamber.

The pressurized gas may be provided by the cleaning device itself and/or by an external device. For instance, the pressure application device may have in particular at least one external pressure connection for connection to an external pressure source. This external pressure source may be, for example, a pressurized gas cylinder formed separately from the cleaning device and/or a pressurized gas line provided on site, for example a compressed air line. Alternatively or in addition, the pressure application device may also have at least one pressurized gas source integrated in the cleaning device. In particular, at least one integrated pressurized gas cylinder may be provided and/or at least one integrated compressor, for providing the pressurized gas. Alternatively or in addition to the provision of an individual pressurized gas, a number of pressurized gases may also be provided at the same time or one after the other.

The cleaning device may, in particular, have at least one holder for receiving the respirator that can be introduced into the cleaning chamber. This holder may be fixedly installed in the cleaning chamber, but may also be movably designed and/or may be designed as a removable holder, which can be taken out of the cleaning chamber, preferably without an additional tool being required for this. The holder may, in particular, be set up for aligning and preferably fixing the respirator in relation to the fluid device. For example, this fixing may be performed in such a way that, although cleaning fluid is applied to the respirator at critical points, the cleaning fluid can preferably flow out from these critical regions after application, for example from concave hollows of breathing masks. The holder may be pivotably designed, so that different positions can be assumed during different steps of a cleaning process. For example, at least one first position may be provided for application of a cleaning fluid, and at least one second position may be provided for emptying of the respirators. The at least one first position may also change during the program, so that application may be performed from a number of directions without the fluid device, for example the nozzles, having to be changed in their position and/or alignment, which however can nevertheless take place. Emptying may be performed, for example, by tilting and/or turning the holder, so that for example breathing masks and/or inner regions of tubes can be emptied. Alternatively or in addition to a holder for fixing the respirator, however, it is also possible in principle for the respirators to be received in the cleaning chamber in a non-aligned and/or non-fixed manner.

Generally, the cleaning device may accordingly be a modified dishwasher and/or a modified laundry washing machine or comprise such a dishwasher or laundry washing machine in a modified state. It is particularly preferred if the cleaning device is set up in such a way that the application of cleaning fluid is performed by jetting, spraying or sprinkling. In particular, the respirator should not be immersed in the cleaning fluid, or at least not completely, during the application, so that, immediately when or immediately after it impinges on the respirator, the cleaning fluid can flow and/or drip off from it again. In this way the cleaning fluid can be prevented from penetrating into the gas carrying element as a result of lengthy exposure or even as result of cleaning fluid being applied to the respirator under excess pressure, and/or residues of the cleaning fluid can be prevented from remaining in the respirator. For example, this is ensured if the cleaning device is designed as a washer in which the respirator is received in a holder and has cleaning fluid applied to it from at least one nozzle, for example from above and/or below the holder, the cleaning fluid being able to flow and/or drip off from the respirator into a washing tank immediately after being applied.

The holder may be designed in particular in such a way that it has a number of different receptacles, which are set up for receiving different types of respirator and/or different component parts of the respirator. In particular, the holder may comprise a number of compartments and/or receptacles, in which different component parts of a respirator can be received and, if necessary, can be fixed and/or spatially aligned, the component parts nevertheless remaining assigned to one another, so that after the cleaning the component parts can be reassigned to one another and joined together without becoming mixed up. For example, the holder may comprise at least two holder groups each with a plurality of receptacles, a holder group being respectively assigned to a respirator and a holder group respectively comprising a number of different types of receptacles for receiving different component parts of the respirator.

If at least one holder is provided, the at least one positive and/or non-positive connecting element described above for the mechanical connection to the respirator that may optionally be provided may, in particular, be fully or partially integrated in the holder. The at least one pressure connection may also be fully or partially integrated in the holder. For example, the pressure connection may comprise one or more connection spigots for connection to the at least one respirator, it being possible for the at least one connection spigot to be connected to further elements of the pressure application device, in particular an integrated and/or external pressurized gas source, by way of one or more central application spigots. For example, a tube connection and/or a pipe connection to the holder may be established, and may be designed for example such that it can be released when the holder is taken out from the cleaning chamber. Alternatively or in addition to integration of the pressure connection in the holder, however, a different type of design of the pressure connection may in principle also be used, for example a simple tube connection to protective breathing masks arranged in any way desired in the cleaning chamber. The holder may, in particular, have a releasable pressurized gas connection to the rest of the cleaning device, in particular to one or more optional other component parts of the pressure application device that are not integrated in the holder. As stated above, the holder and/or the pressure connection and/or other component parts of the pressure application device may, for example, comprise at least one pressure distributor, by means of which pressurized gas can be distributed among a number of respirators and/or a number of gas carrying elements, in particular from the at least one optional releasable pressurized gas connection as a central pressure connection and as a central connection to the remaining cleaning device. The pressure distributor may, for example, comprise a number of connections for gas carrying elements, for example in a linear and/or stellar arrangement.

As stated above, the cleaning device may, in particular, be set up as an automatic programmed washer, in order to carry out a cleaning program with one or more program steps. In particular, the cleaning device may be set up for carrying out a cleaning program with at least two different program steps. For example, different program steps allow different types of cleaning fluids to be applied, for example at least one cleaning step in which a cleaning agent solution is applied, and at least one further program step, in particular a post-rinsing step, in which a post-rinsing fluid is applied. Optionally, if necessary at least one program step that takes the form of a drying step may also be provided, it being possible if necessary for the drying to be performed passively, for example by simple dripping off, or alternatively in a way in which the drying can also be actively assisted, for example by automated blowing out of the masks with compressed air and/or by providing a heat source such as hot air, microwaves and/or at least one similar heat source or drying source.

Further possible designs concern the fluid device. As stated above, the fluid device may, in particular, have at least one nozzle. In particular, it may be a nozzle which is selected from a spraying nozzle, a rinsing nozzle, a spraying arm, in particular a pivotable spraying arm, and a nozzle that can be operated in a circulating mode. A combination of the types of nozzles mentioned and/or other types is also conceivable. Alternatively or in addition, the fluid device may, however, also for example comprise a simple opening for letting the cleaning fluid into the cleaning chamber.

The cleaning fluid may, in particular, comprise an aqueous cleaning fluid, that is to say water or water with the addition of one or more additives, which may be in a dissolved form, in the form of an emulsion or else in the form of a suspension. Alternatively or in addition, the cleaning fluid may also comprise at least one cleaning agent solution. A cleaning agent solution should be understood in this case as meaning generally a solution of at least one surfactant in at least one solvent, for example likewise water. For example, here it may be a commercial cleaning agent solution that can also be used for dishwashers and/or that can be used in washing machines. However, in principle special cleaning agent solutions may also be developed and/or used. Once again alternatively or in addition, the cleaning fluid may also comprise a cleaning fluid with at least one rinse aid, that is to say an additive which makes it easier for the respirator to dry off and/or makes it easier for liquid to roll off in drops from at least one surface of the respirator. Such rinse aids, which may likewise comprise one or more surfactants, are known in principle from the area of dishwasher technology. Once again alternatively or in addition, the cleaning fluid may also comprise at least one post-rinsing fluid, which may, for example, in principle be water and/or water with one or more additives. Once again alternatively or in addition, the cleaning fluid may also comprise a cleaning fluid with at least one disinfectant, where disinfectant may be understood in principle as meaning any desired substance that has a germicidal effect. Such disinfectants are likewise known in principle from the prior art. Once again alternatively or in addition, the cleaning fluid may also comprise demineralized water. As explained in more detail below, the demineralized water may, for example, be provided in a corresponding demineralizing device of the cleaning device, for example an ion exchanger. Alternatively or in addition, the demineralizing device may, however, also comprise a reverse osmosis device. Once again alternatively or in addition, the cleaning fluid may also comprise a heated cleaning fluid. Such heated cleaning fluids may be suitable in particular for post-rinsing, where heated cleaning fluids should be understood in principle as meaning cleaning fluids that have a temperature of at least 25° C. Particularly preferred are temperatures of 30° C. to 70° C. and in particular 60° C. These temperatures have proven to be suitable in particular for the cleaning of flexible elastomer materials, as are often used for respirators.

As explained above, the provision of high-quality cleaning fluids is of particular importance for the cleaning of respirators. In this way, for example, microscopic or macroscopic contamination of the respirators can be avoided. Microscopic contaminants, such as for example mineral contaminants, cause for example limescale deposits on viewing surfaces, such as for example lenses of the respirators. Furthermore, microbial contaminants may lead to contamination of the respirators. It is therefore particularly preferred if the cleaning device has at least one reverse osmosis device for providing water, in particular demineralized water. A reverse osmosis device should be understood as meaning generally a device that can provide a fluid with a high degree of purity, using the principle of reverse osmosis. For example, the reverse osmosis device may have one or more osmosis membranes, through which clean constituents of the water can be forced under high pressure, so that a cleaned permeate is obtained, whereas contaminants remain behind on a concentrate side. For example, pressures of above 2 bar, in particular above 5 bar, may be used here.

As explained above, particularly commercially obtainable laundry washing machines and/or dishwashers, for example industrial laundry washing machines and/or industrial dishwashers, may be converted in accordance with these teachings. This conversion may be performed by the laundry washing machines or dishwashers being equipped with a pressure application device according to the features described above. The cleaning device may, for example, be designed as a front-loader washer or as a hood-type washer. A front-loader washer should be understood here as meaning a washer with a cleaning chamber which can be opened by a user standing in front of the washer using a flap and/or a slide. A hood-type washer should be understood in this case as meaning a washer of which the cleaning chamber comprises a hood that can be swung up and/or moved up and can be separated from other component parts of the cleaning chamber, for example a base. Such hood-type washers are known in principle from the area of industrial dishwasher technology. The cleaning chamber may, in particular, be of a rigid design. The cleaning chamber may generally be designed such that it can be locked during the cleaning process, in particular by being provided with an automatic locking mechanism, which is preferably triggered during a program and can be automatically released again after a program.

In a further aspect of this disclosure, a holder for use in a cleaning device according to one or more of the aforementioned designs is disclosed. Accordingly, for possible designs of the holder, reference can be made to the above description, and there in particular to the features concerning the holder. It is intended that the holder can be introduced into the cleaning chamber. It may be introduced permanently or else reversibly, for example by the holder having at least one connecting element for connection to the cleaning chamber. For example, the holder may comprise one or more rollers and/or wheels and/or other types of connecting elements that can be pushed into one or more rails within the cleaning chamber. Other designs of the connecting elements are also possible.

The holder is set up for receiving at least one respirator. Preferably, the holder is also set up for aligning the respirator in relation to the fluid device. The alignment may in this case be performed completely or partially, for example in that only part of the respirator is aligned in relation to one or more nozzles, so that cleaning fluid can be routinely and reliably applied to particularly critical parts. The alignment may in this case take place rigidly or else, as stated above, movably, for example pivotably and/or rotatably. For example, the cleaning device may be designed in such a way that different positions and/or different alignments of the respirator are provided in different program steps. The holder has at least one integrated pressure connection, it being possible for the pressure connection to act as a component part of the pressure application device and the pressure connection being set up for being connected to at least one gas carrying element of the respirator. As stated above, at least one mechanical connecting element may be additionally provided, for example a positive and/or non-positive connecting element, which can establish a mechanical connection between the holder and the respirator. In particular, at least one quick coupling and/or at least one thread may be provided within the holder. For further possible designs of the holder, which may for example be designed as an accessory part and/or as an exchangeable part, reference is made to the above description. In particular, the holder may be loaded with one or more respirators outside the cleaning chamber before the loaded holder can be introduced into the cleaning chamber. Various designs are possible.

The cleaning device described above can be advantageously used in various ways. In particular, it is accordingly proposed to use the cleaning device in one or more of the designs explained above for cleaning at least one respirator, it being possible for the respirator to be selected in particular from: a breathing regulator or a breathing mask for divers; a breathing regulator or a protective breathing mask for members of rescue teams; a compressed air breathing apparatus; a breathing regulator or a protective breathing mask for members of the police or military forces or other security forces; and a breathing regulator or a breathing mask for medical purposes. However, other uses are also possible in principle.

In a further aspect of these teachings, a method for cleaning a respirator is proposed. In particular, it may be a breathing regulator and/or a breathing mask, for example a protective breathing mask. In particular, as explained above, the respirator may comprise at least one region with at least one valve by which an inner space, for example a gas carrying inner space of a gas carrying element, can be separated from an outer space, it being possible in particular for the method to be carried out in such a way that cleaning fluid is not applied in the inner space. In particular, this valve may be at least one rocker arm of a breathing regulator. However, other designs are also possible in principle. The method may be carried out in particular using a cleaning device according to one or more of the designs described above, so that reference can be made to the above description with respect to optional designs. However, other cleaning devices can also be used in principle and/or the method can also be carried out manually.

In the case of the method, at least one cleaning fluid is applied to the respirator. During the application of the cleaning fluid, pressurized gas is applied to at least one gas carrying element of the respirator. The application of the pressurized gas may, in particular, be performed in such a way that substantially no cleaning fluid can penetrate into the interior of the gas carrying element, for example by suitably choosing the throughput and/or the pressure of the pressurized gas. It may be here that penetration is prevented completely. Alternatively, however, it may also be that small amounts, for example small amounts in the microliter range or nanoliter range, are tolerated.

The cleaning device described above, the holder described above, the use and the proposed method have many advantages over known methods and devices. For instance, a short cleaning time, for example within a cleaning program, can be realized in particular, with at the same time a high cleaning performance and low consumption of energy and water. This can be realized in particular by means of a washing machine or a washer that operate on what is known as the two-circuit principle, similar to the embodiments such as are known in the industrial washing of dishes, for example in the form of single-chamber automatically programmed washers. Conceivable versions of this are, for example, front-loader or hood-type models.

The use of a holder, in particular a removable holder, for the respirators makes it possible for example to fasten one or more respirators, for example protective breathing masks, in a way that on the one hand all surfaces are reached and on the other hand the cleaning fluid runs off well. For example, positioning in relation to the spray jets and/or other fluid devices may be performed, so that all critical surfaces can be reached well by the cleaning fluid. On the other hand, it can be achieved by suitable alignment that no accumulations of remains of cleaning fluid can form inside the respirators, for example inside masks. For example, the holder may be designed for receiving two, three, four, five or more respirators, for example for receiving such a number of breathing masks and/or breathing regulators. The holder, of which a number may also be provided, may in particular be designed in such a way that accessories of the respirators can in each case remain assigned to a respirator. For example, accessories can be assigned to an individual breathing mask, for example in that the holder comprises a rack-like container in which the accessory can be received. In this way, the assignment is also retained during the cleaning process.

The cleaning device, and in particular the holder, may in particular be equipped with one or more pressure connections for the respirator, for example for one or more breathing regulators, it being possible for gas at a positive pressure, for example compressed air, to be carried by means of the at least one pressure connection. During the loading of the cleaning device, the breathing regulator or regulators can be coupled by its or their gas carrying region to this at least one pressure connection. The coupling operation allows the entire gas carrying region or part of the same for the at least one respirator, for example the breathing regulator, to be flooded by the gas, which may be under higher pressure than the ambient pressure. Cleaning fluid is thus reliably prevented from penetrating into the at least one gas carrying region during the process of cleaning the remaining surfaces.

The pressurized gas for the pressure application device may be supplied in various ways. For instance, a connection to the cleaning device may be created by a pressurized gas connection provided on site. Alternatively or in addition, at or within the cleaning device there may be provided a pressurized gas container, which after it has been emptied may for example be exchanged for a full container. Once again alternatively or in addition, in the cleaning device there may also be provided at least one compressor, which can for example generate pressurized gas, in particular compressed air, directly in situ.

A use of the cleaning device as intended may, for example, take the form that first the at least one respirator, for example protective breathing masks, accessories and breathing regulators, are fastened to the holder as prescribed. Then, the entire holder may optionally be introduced into the cleaning chamber, for example the washing chamber of the washer. Optionally, a pressurized gas connection may be established with the holder before, during or after the holder is introduced. The cleaning chamber may then be closed, and a cleaning program started. For example, the cleaning program may take the form that, in a first step, the respirator is rinsed off and/or bathed for a certain time with a cleaning fluid, for example a cleaning liquid. The cleaning fluid may, for example, be water-based and may be mixed with one or more additives. These additives may be comparable to cleaning agents that are currently used for the manual cleaning of protective breathing masks. The additives may be made to match the materials of which the protective breathing masks are made. Furthermore, the cleaning fluid may contain one or more components that bring about a chemically based disinfection, that is to say one or more disinfectants. The cleaning fluid may be heated, for example to 60° C. The temperature may, in particular, be made to match the requirements of the materials of which the respirator is composed, for example the requirements of the materials of the masks, and/or may, for example, result from requirements of the cleaning agents and/or disinfectants that are used. In a further program step, the at least one respirator may optionally be after-rinsed with a post-rinsing fluid, for example fresh water. The post-rinsing fluid may, for example, likewise be heated and/or mixed with a rinse aid, which may promote the running off of the fluid and the drying. Particular advantages for the post-rinsing effect are obtained if the fresh water is demineralized, for example using the osmosis system described above. Optionally, the cleaning may also be divided into a number of steps, or a number of post-rinsing steps may be performed. The duration of the individual program steps may likewise be adapted to the requirements, for example requirements of the cleaning agents and/or disinfectants that are used and/or the type of respirators and/or a degree of contamination or soiling. Programming times of 5 minutes are known, for example, for successfully carrying out a chemo-thermal disinfection. At the end of a cleaning program, the holder with the at least one cleaned and optionally hygienized respirator may then optionally be removed from the cleaning chamber, for example the rinsing chamber. After a short waiting time, which may pass with the item inside or outside the cleaning chamber, generally all remains of liquid have dripped off or dried off from the respirator. The respirator can then be taken off the holder, and further preparational steps may follow. Optionally, the cleaning chamber may be manually or automatically locked by a machine controller during the cleaning program and be released at the end of a properly performed program sequence for the removal of the respirator.

The described cleaning device and the proposed method may also be used at other places where respirators, for example breathing masks and particularly breathing regulators, are used. For example, disaster control has already been mentioned above, as well as military forces, recreational diving and certain areas of medicine. In these and in other areas, the advantages of the proposed cleaning device and of the proposed method are noticeable particularly favorably. These advantages consist particularly in a small amount of time that has to be expended for cleaning the respirator and its accessories. While an automatic cleaning program can be running, an operator can perform further activities involved in the preparation of the respirator, for example mask preparation, so that an efficient working procedure can be obtained. The specific way in which the respirator, for example the masks, is/are received, and the good running off of cleaning fluid brought about as a result, allows the time for the drying process that is subsequently generally prescribed to be reduced drastically. The proposed method and the proposed cleaning device consequently make it possible for respirators, including one or more breathing regulators, to be cleaned in a way that is efficient and nevertheless dependable. The cleaning process may in this case be standardized and monitored, whereby a consistently high quality of cleaning and level of hygiene can be ensured in particular. For the users of the respirator, this means that they can have greater confidence in their personal protective equipment. At the same time, a standardized method ensures use of less resources than in the case of conventional methods, in particular than in the case of manual cleaning methods.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
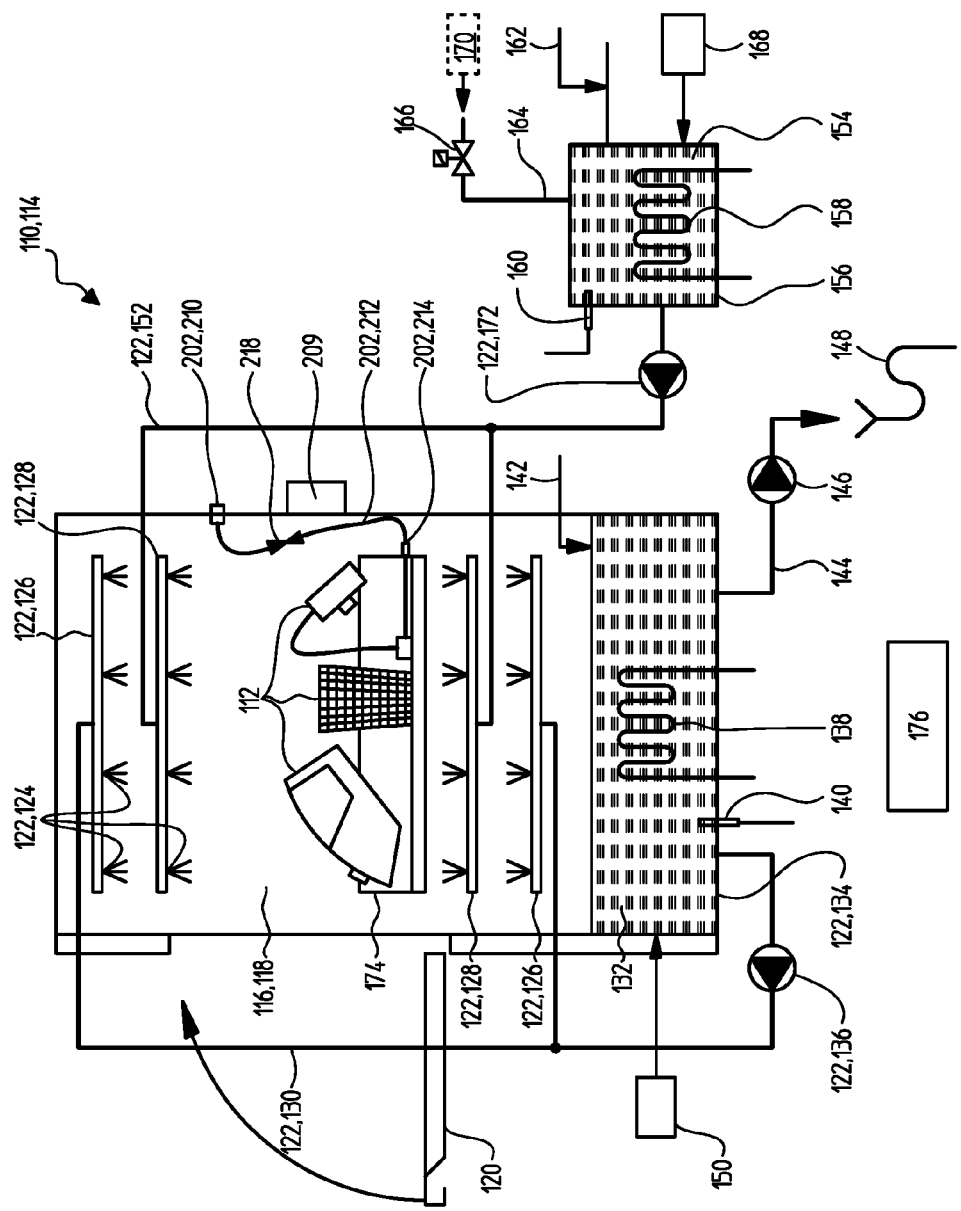
FIG. 1 shows a sectional representation of an exemplary embodiment of a cleaning device according to this disclosure.

Represented in FIG. 1 is an exemplary embodiment of a cleaning device 110 that is set up for cleaning one or more respirators 112. In FIG. 1, the cleaning device 110 is schematically shown in a sectional representation. The cleaning device 110 may, for example, be designed as a washer 114. The cleaning device 110 comprises a cleaning chamber 116, for example a rinsing chamber 118. This cleaning chamber 116 may, for example, be opened by means of a door 120, for example a hinged door, a sliding door or a flap, and/or by means of some other opening device. Alternatively or in addition, the cleaning chamber 116 may also be designed as a cleaning chamber covered by a hood. Other designs are also possible. In the exemplary embodiment represented in FIG. 1, the washer 114 is, for example, designed as a front-loader washer. However, other designs are also possible.

The cleaning device 110 has at least one fluid device 122 for applying one or more cleaning fluids to the respirators 112 received in the cleaning chamber 116. For example, the fluid device 122 may comprise one or more nozzles 124, which may, for example, be arranged above and/or below the respirators 112 and/or at different locations within the cleaning chamber 116, for example on one or more side walls. For example, as in the exemplary embodiment presented according to FIG. 1, the fluid device 122 may comprise a washing nozzle system 126, for example with one or more nozzle arms that are accommodated below and/or above the respirators 112, preferably rotatably and/or pivotably mounted, and have a number of nozzles 124. Alternatively or in addition, the fluid device 122 may also comprise a post-rinsing nozzle system 128, for example with one or more post-rinsing nozzle arms, which are preferably once again mounted rotatably and/or pivotably, and once again may, for example, be arranged above and/or below the respirators 112. However, other arrangements and/or designs are also possible in principle.

The fluid device 122 may additionally comprise one or more further elements, such as for example one or more pipelines, one or more pumps and/or one or more tanks. For example, in the exemplary embodiment represented, at least one washing line system 130 is provided, for applying cleaning fluid 132, for example cleaning agent solution, to the washing nozzle system 126 from one or more washing tanks 134. For example, a washing tank 134 may be provided in the bottom region of the cleaning chamber 116 and/or be connected in some other way to the cleaning chamber 116, so that, after being applied to the respirators 112, cleaning fluid 132 can flow and/or drip back again into the washing tank 134. For applying the cleaning fluid 132 to the washing nozzle system 126 from the washing tank 134, the fluid device 122 may also have one or more circulating pumps 136. Furthermore, one or more heating elements 138 may be provided, in order to heat the cleaning fluid 132 of the washing tank 134 and/or other tanks, for example in the form of a washing tank heater within the washing tank 134. For checking the heating up of the cleaning fluid 132, one or more temperature sensors 140 may be provided, for example within the washing tank 134. Furthermore, one or more level sensors 142 may be provided, for example a level sensor 142 as a level sensor of the washing tank 134. The washing tank 134 may be drainable, for example by way of a discharge line 144 and optionally by way of a discharge pump 146, into a discharge 148. One or more feeds, not represented in FIG. 1, to the washing tank 134 may also be optionally provided, in order to fill said tank with cleaning fluid 132. Alternatively or in addition, however, filling may also be performed by way of the post-rinsing nozzle system 128 described in more detail below. Furthermore, a metering system 150 may be provided, for example at least one metering system for introducing one or more additives into the cleaning fluid 132 of the washing tank 134, for example a cleaning agent concentrate, a rinse aid, a disinfectant or a combination of the additives mentioned and/or other additives.

The cleaning fluid 132 may, in particular, be applied to the respirators 112 in a circulating operating mode, in that the cleaning fluid 132 from the washing tank 134 is sprayed and/or squirted onto the respirators 112 by way of the washing nozzle system 126, to then dry off or run off again into the washing tank 134, to be re-used from there. Optionally, one or more filters, for example coarse filters and/or fine filters, may be provided, for at least partially cleaning the cleaning fluid 132 of the washing tank 134.

A further cleaning fluid 154, for example a post-rinsing liquid, may be applied to the post-rinsing nozzle system 128, for example by way of at least one post-rinsing line system 152. In this respect, an optional design in which the cleaning device 110 is designed as a two-circuit system is shown in FIG. 1. Accordingly, the second cleaning fluid 154 is provided from a separate tank, which in the exemplary embodiment represented is designed as a post-rinsing tank 156, which is formed separately from the washing tank 134. For example, this post-rinsing tank 156 may be designed as a boiler and may, for example, comprise a post-rinsing tank heater 158. Alternatively or in addition to a post-rinsing tank heater 158, other types of heating elements may also be provided for the second cleaning fluid 154, for example one or more continuous heaters. The same also applies to the first cleaning fluid 132 in the washing tank 134. Once again, one or more temperature sensors 160 and/or one or more level sensors 162 may be provided in the post-rinsing tank 156, and the post-rinsing tank 156 may be charged with cleaning fluid 154, for example fresh water, by way of one or more feeds 164. The at least one feed 164 may have one or more valves 166. For example the feed 164 may be connected or able to be connected to a fresh water connection provided on site. Alternatively or in addition, at least one reverse osmosis device 170 may be provided, on site or as a component part of the cleaning device 110, and be used as a way of applying a permeate, for example cleaned water, to the post-rinsing tank 156 and/or one or more other tanks of the cleaning device 110. Furthermore, once again at least one metering system 168 may be provided, and be used as a way of being able to admix one or more additives, for example one or more rinse aid concentrates, with the cleaning fluid 154 in the post-rinsing tank 156.

The application of the fluid to the post-rinsing nozzle system 128 may be performed in the simple operating mode, that is to say not in the circulating operating mode, so that the post-rinsing fluid from the post-rinsing tank 154 is only applied once to the respirator 112. For the application, the fluid device 122 may, for example, comprise one or more pressure increasing pumps 172.

The cleaning of the respirators 112 in the cleaning device 110 according to FIG. 1 may be performed for example by first introducing one or more respirators 112 into the cleaning chamber 116 by means of a suitable holder 174, which is explained in more detail below. The door 120 may then be closed, and preferably a cleaning program started, which program can be controlled for example by way of a controller 176, for example a central machine controller or a decentralized controller. This may, for example, involve first the washing tank 134 being filled by means of the post-rinsing nozzle system 128 with cleaning fluid 132 and/or a preliminary stage of this cleaning fluid 132, for example fresh water, in particular demineralized fresh water. This may then be conditioned within the washing tank 134, for example by admixing one or more additives by way of the metering system 150 and/or by heating by means of the heating element 138. Alternatively or in addition, the cleaning fluid 132 may also remain in the washing tank 134 after a final rinsing program of a preceding cleaning cycle, to be used in a subsequent cleaning cycle as a cleaning fluid 132 and/or as a constituent of the same, since post-rinsing fluid generally has a comparatively high degree of purity even after being applied to the respirator 112.

Then, the respirator 112 may be cleaned, in particular washed, preferably in a circulating operating mode, in one or more washing program steps. This may involve removing adhering contaminants from the respirators 112, and/or may involve hygienization of the respirators 112.

Following the at least one washing program step, one or more post-rinsing steps may preferably be carried out. For this purpose, the washing tank 134 may optionally be drained by way of the discharge line 144 and the discharge pump 146. Already during the at least one washing program step, the post-rinsing tank 156 may have been filled with the post-rinsing fluid 154, for example fresh water with or without additives, for example demineralized fresh water.

Then, one or more additives may be admixed by way of the metering system 150 and/or heating of the cleaning fluid 154 as a post-rinsing fluid may be performed by means of the post-rinsing tank heater 158 and/or a continuous heater. The post-rinsing fluid 154 preconditioned in this way may then be applied to the respirators 112 by way of the post-rinsing nozzle system 128 in the at least one post-rinsing step, so that they undergo post-rinsing and/or final rinsing. After the at least one post-rinsing step, there may optionally follow once again at least one drying step, which may be of a passive kind, performed by simply waiting, or which may also be actively assisted, for example by way of at least one drying blower and/or some other type of drying device of the cleaning device 110, for example an infrared emitter system and/or a microwave radiation system. Various designs are conceivable. The optional drying step may be followed by the, until then optionally and preferably, locked door 120 being automatically released and/or opened. The entire program sequence may, for example, be controlled by the controller 176, it also being possible for a number of program sequences to be selectable.

It is pointed out that the exemplary embodiment of the cleaning device 110 that is represented in FIG. 1 merely represents one of a number of different exemplary embodiments. Thus, one or more or all of the elements described above may also be implemented in a different framework. The rinsing chamber 118 may, as an alternative or in addition to the rigid, fixed-in-place design according to FIG. 1, also be of a pivotable and/or rotatable design. Furthermore, the fluid circuit represented may also be modified considerably.

Figure 2:
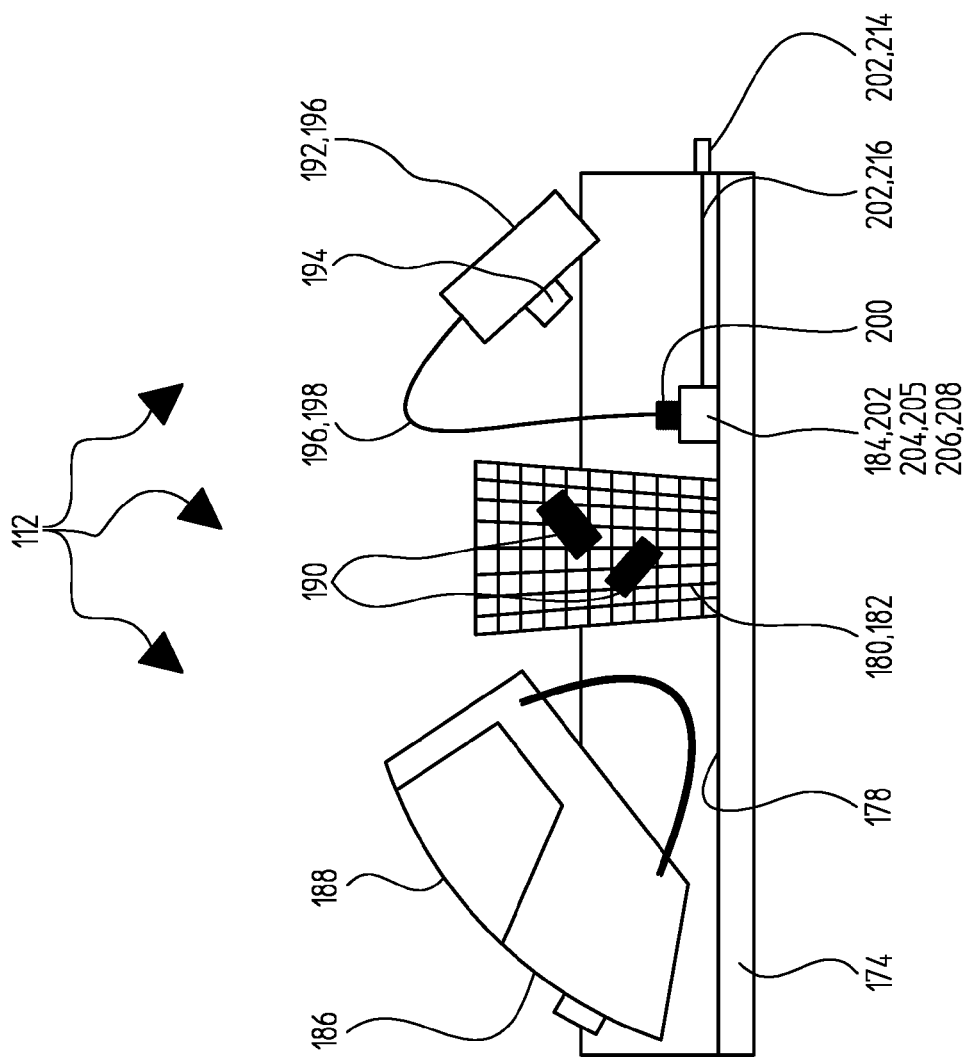
FIG. 2 shows a representation of a detail of a loaded holder of the cleaning device according to FIG. 1.

As explained above, the at least one respirator 112 is held within the cleaning device 110, preferably by means of at least one holder 174. In FIG. 2, such a holder 174 is shown by way of example in an enlarged and sectional representation. The holder 174 may, for example, be produced from plastic and/or metal and may, for example, be designed as a rack, as shown in FIG. 2. The holder 174 may comprise one or more supporting surfaces 178 and/or one or more holding elements 180, for example one or more racks 182 and/or one or more connecting elements 184 for a mechanical connection to the respirator 112 and/or the fixing thereof. Accordingly, the holder 174 may, for example, be designed for aligning and/or fixing one or more components of the respirator 112 in relation to one or more of the nozzles 124. For example, the respirator 112 may comprise at least one breathing mask 186, the alignment by the supporting surface 178 taking place for example in such a way that a lens 188 is always facing the upper nozzle system, whereas the inner side of the breathing mask 186 faces downward, so that cleaning fluid 132, 154 entering by way of the lower nozzles can run off again after it has been applied, without residues remaining within the breathing mask 186. The rack 182 may, for example, be set up for receiving accessories 190, which may likewise be a component part of the respirator 112, for example for maintaining an assignment to other components of the respirator 112 during the cleaning process. In this way it can be ensured, for example, that different types of respirators 112 can be cleaned without incompatible accessory parts getting mixed up. Furthermore, the respirator 112 may, for example, comprise one or more breathing regulators 192 and/or one or more stages of such breathing regulators 192. Such breathing regulators 192 generally comprise inside them one or more valves 194, for example membrane valves and/or rocker arm valves, by way of which one or more gas carrying elements 196 are separated from an outer space. For example, gas carrying elements 196 may be provided inside one or more gas lines 198 of the breathing regulator 192, the inner walls of the gas line 198 generally not being allowed to come into contact with cleaning fluid 132, 154. The gas line 198 may, for example, end in one or more connections 200, for example in one or more quick couplings.

In order to prevent the at least one gas carrying element 196 of the respirators 112, for example the gas line 198 of the breathing regulator 192, from coming into contact with cleaning fluid 132, 154, it is envisaged to apply pressurized gas to this gas carrying element 196, for example during one or more program steps in which the cleaning fluid 132, 154 is applied to the respirator 112. For this purpose, the cleaning device 110 has in this or else in other exemplary embodiments at least one pressure application device 202. This pressure application device 202 is set up for applying pressurized gas to the at least one gas carrying element 196. For this purpose, the pressure application device 202 has at least one pressure connection 204, which can be connected to the gas carrying element 196 in such a way that such an application of gas can be performed. In the exemplary embodiment represented, this pressure connection 204 is formed by way of example as a component part of the holder 174. Alternatively or in addition, however, the pressure connection 204 may also be provided at other locations of the cleaning device 110, preferably inside the cleaning chamber 116. The pressure connection 204 may be designed, for example in the exemplary embodiment represented, as a connection 206 for the breathing regulator 192. In this or else in other exemplary embodiments, the pressure connection 204 may generally be designed in such a way that it can be connected to different types of gas carrying elements 196, for example to different types and/or different kinds of gas carrying elements 196. For example, the pressure connection 204 may comprise a plurality of adapters 205 and/or the cleaning device 110 may be supplied along with a set of adapters comprising a number of adapters 205 of various pressure connections 204, so that there is a high degree of flexibility with regard to the type of gas carrying elements 196. For example, the connection 206 for the breathing regulator 192 may comprise a quick coupling which corresponds to the connection 200 of the gas line 198 and can be connected to it, preferably in a pressure-tight manner. In this or else in other cases, the pressure connection 204 may consequently also comprise at least one connecting element 208 and/or be designed as a connecting element 208 for establishing a mechanical connection to the respirator 112, and in particular the gas carrying element 196.

For applying pressurized gas, for example compressed air, to the pressure connection 204 and the gas carrying element 196, the cleaning device 110 in the exemplary embodiment represented or else in other designs may comprise at least one internal and/or at least one external pressurized gas source. An optional integrated pressurized gas source 209, which is indicated in FIG. 1, may, for example, comprise at least one compressor and/or at least one pressurized gas cylinder. Alternatively or in addition, as represented in FIG. 1, the cleaning device 110 may also be equipped with at least one external pressure connection 210, in order to be connected by way of this external pressure connection 210 to at least one external pressurized gas source, for example an external pressurized gas cylinder and/or an external pressurized gas line, which may be provided for example in the building. The external pressure connection 210 and/or the internal pressurized gas source may, for example, be connected to the pressure connection 204 by way of at least one pressurized gas line 212. If the pressure connection 204 is connected to the holder 174, as represented in FIGS. 1 and 2, the pressurized gas line 212 may, for example, be releasably connected to the holder 174 and/or the pressure connection 204, in order to make it optionally possible for the holder 174 to be reversibly taken out from the cleaning device 110. For example, one or more couplings 214, which once again may, for example, be connected to the pressure connection 204 by way of one or more pressurized gas lines 216, may be provided for this purpose. A distributor system may also be provided inside or outside the holder 174, for example to allow pressurized gas to be applied to a plurality of pressure connections 204 by means of a pressurized gas line 212. Once again, one or more adapters 205 may also be provided, for example to make it possible to adapt to a plurality of different types of gas carrying elements 196 and/or respirators 112. The pressure application device 202 may be designed such that it can be separated at one or more points, for example in order to be able to remove the holder 174 from the cleaning chamber 116 and for example load it. For this purpose, the coupling 214 may, for example, be of a releasable design. Furthermore, in this or else in other exemplary embodiments of the cleaning device 110, the pressure application device 202 may optionally comprise one or more valves 218, for example controllable valves, for example (as represented in FIG. 1) in the pressurized gas line 212 and/or in or upstream of the external pressure connection 210. These valves 218 may be controlled for example by the controller 176. For example, in this or else in some other way, the application of pressure to the at least one gas carrying element 196 by means of the pressure application device 202 may in this or else in other exemplary embodiments be performed in a controlled manner, for example in that the pressure is applied specifically before any application of cleaning fluid 132, 154 to the respirators 112. Alternatively or in addition, the application of pressure may also take place only in one or more program steps, for example only in one or more program steps while cleaning fluid 132, 154 is being applied to the respirators 112. By contrast, the application of pressurized gas, for example compressed air, may optionally be switched off and/or take place in a different form, for example with changed pressure, during other program steps. In this way, the application of pressure can, for example, be adapted to the various program steps.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERAL DESIGNATIONS

| | |
|---|---|
| 110 | Cleaning device |
| 112 | Respirators |
| 114 | Washer |
| 116 | Cleaning chamber |
| 118 | Rinsing chamber |
| 120 | Door |
| 122 | Fluid device |
| 124 | Nozzles |
| 126 | Washing nozzle system |
| 128 | Post-rinsing nozzle system |
| 130 | Washing line system |
| 132 | Cleaning fluid, washing fluid |
| 134 | Washing tank |
| 136 | Circulating pump |
| 138 | Heating element |
| 140 | Temperature sensor |
| 142 | Level sensor |
| 144 | Discharge line |
| 146 | Discharge pump |
| 148 | Discharge |
| 150 | Metering system |
| 152 | Post-rinsing line system |
| 154 | Cleaning fluid, post-rinsing fluid |
| 156 | Post-rinsing tank |
| 158 | Post-rinsing tank heater |
| 160 | Temperature sensor |
| 162 | Level sensor |
| 164 | Feed |
| 166 | Valve |
| 168 | Metering system |
| 170 | Reverse osmosis device |
| 172 | Pressure increasing pump |
| 174 | Holder |
| 176 | Controller |
| 178 | Supporting surface |
| 180 | Holding element |
| 182 | Rack |
| 184 | Connecting element |
| 186 | Breathing mask |
| 188 | Lens |
| 190 | Accessory |
| 192 | Breathing regulator |
| 194 | Valve |
| 196 | Gas carrying element |
| 198 | Gas line |
| 200 | Connection |
| 202 | Pressure application device |
| 204 | Pressure connection |
| 205 | Adapter |
| 206 | Connection for breathing regulator |
| 208 | Connecting element |
| 209 | Integrated pressurized gas source |
| 210 | External pressure connection |
| 212 | Pressurized gas line |
| 214 | Coupling |
| 216 | Pressurized gas line |
| 218 | Valves |

What is claimed is:

1. A method for cleaning a respirator using a cleaning device having a chamber for receiving a respirator, a holder that is removably insertable in the chamber, a pressure application device, and a fluid device, the method comprising:

inserting the respirator into the holder;
connecting a gas carrying element of the respirator to a pressure connection of the pressure application device;
inserting accessory parts into a basket supported by the holder;
introducing the holder into the cleaning chamber;
applying pressurized gas to the gas carrying element; and executing a cleaning program which includes applying a cleaning fluid to the respirator and the accessory parts with the fluid device.

2. The method of claim 1, wherein the cleaning program has at least two different program steps.

3. The method of claim 2, wherein one program step is a cleaning step with an aqueous solution of a detergent that has cleaning and disinfecting ingredients.

4. The method of claim 2, wherein the second program step is a rinsing step with an aqueous solution of rinse aid.

5. The method of claim 1, further comprising connecting the pressure application device to a pressurized gas line and/or a pressurized gas cylinder.

6. The method of claim 1, further comprising heating cleaning fluid disposed in a fluid tank of the cleaning device and independently conducting a cleaning process in the cleaning device.

7. The method of claim 1, further comprising drying the respirator within or outside the cleaning chamber.

8. The method of claim 1, wherein the application of pressurized gas takes place during the cleaning program.

9. The method of claim 1, wherein the connection of the gas carrying element to the pressure connection prevents the cleaning fluid from penetrating the gas carrying element during the execution of the cleaning program.

10. The method of claim 9, further comprising providing a gas-tight and liquid-tight connection between the gas carrying element and the pressure connection.

11. The method of claim 10, further comprising maintaining positive gas pressure in the gas carrying element during the execution of the cleaning program.

12. The method of claim 1, wherein the cleaning program has multiple steps and the step of applying pressurized gas to the gas carrying element is performed during at least one step of the cleaning program.

13. The method of claim 12, wherein the step of applying pressurized gas to the gas carrying element takes place during all steps of the cleaning program.

14. A method for cleaning a respirator using a cleaning device having a chamber for receiving a respirator, a holder that is removably insertable in the chamber, and a pressure application device, the method comprising:
(a) positioning a breathing mask and a gas carrying element of the respirator separately from one another in the holder;
(b) connecting the gas carrying element of the respirator to a pressure connection of the pressure application device;
(c) introducing the holder into the cleaning chamber;
(d) applying pressurized gas to the gas carrying element; and
(e) applying a cleaning fluid to the breathing mask and the gas carrying element.

15. The method of claim 14, wherein steps (d) and (e) are performed at the same time.

16. The method of claim 14, wherein step (d) begins before step (e).

17. The method of claim 14, wherein the connection of the gas carrying element to the pressure connection established in step (b) prevents the cleaning fluid from penetrating the gas carrying element during step (e).

18. The method of claim 17, further comprising providing a gas-tight and liquid-tight connection between the gas carrying element and the pressure connection.

19. The method of claim 14, further comprising connecting the pressure application device to a pressurized gas line and/or a pressurized gas cylinder.

20. The method of claim 14, further comprising carrying out a cleaning program including step (e) and at least one additional program step.

21. The method of claim 14, further comprising selecting an adaptor to connect the gas carrying element to the pressure connection.

22. The method of claim 14, wherein the connecting of the gas carrying element of the respirator of step (b) takes place during the introducing of the holder into the cleaning chamber of step (c).

23. The method of claim 14, wherein step (e) is performed with a nozzle that sprays, sprinkles or jets the cleaning fluid.

24. The method of claim 23, wherein the nozzle comprises two nozzles and step (e) is performed with one of the nozzles positioned below the respirator and the other nozzle positioned above the respirator.

25. The method of claim 23, further comprising using the holder to align the respirator with the nozzle.

26. The method of claim 23, further comprising rotating a nozzle arm during step (e).

27. The method of claim 14, wherein the gas carrying element is a breathing regulator.

28. The method of claim 1, wherein the basket has an open top.

29. The method of claim 1, further comprising separately inserting a breathing mask and the gas carrying element of the respirator into the holder.

30. The method of claim 29, further comprising placing the breathing mask and the gas carrying element in different locations in the holder.

31. The method of claim 29, further comprising placing the breathing mask, gas carrying element and auxiliary parts in different locations in the holder.

32. The method of claim 14, further comprising placing the breathing mask and the gas carrying element in different locations in the holder.

33. The method of claim 14, further comprising inserting auxiliary parts into a basket of the holder.

34. The method of claim 33, wherein the basket has an open top.

35. The method of claim 33, further comprising placing the breathing mask, gas carrying element and auxiliary parts in different locations in the holder.

* * * * *